United States Patent
Ha et al.

(10) Patent No.: US 7,238,836 B2
(45) Date of Patent: Jul. 3, 2007

(54) METHOD OF PRODUCING UNSATURATED ALDEHYDE AND UNSATURATED ACID IN FIXED-BED CATALYTIC PARTIAL OXIDATION REACTOR WITH ENHANCED HEAT CONTROL SYSTEM

(75) Inventors: Kyoung Su Ha, Seoul (KR); Geon Yong Kim, Gwangju (KR); Seong Pil Kang, Daejeon (KR); Seok Hwan Choi, Daejeon (KR); Boo Gon Woo, Daejeon (KR)

(73) Assignee: LG Chem, Ltd., Seoul (KR)

( * ) Notice: Subject to any disclaimer, the term of this patent is extended or adjusted under 35 U.S.C. 154(b) by 388 days.

(21) Appl. No.: 10/931,034

(22) Filed: Sep. 1, 2004

(65) Prior Publication Data

US 2005/0049435 A1    Mar. 3, 2005

(30) Foreign Application Priority Data

Sep. 1, 2003    (KR)    ............ 10-2003-0060736

(51) Int. Cl.
  C07C 51/16    (2006.01)
  C07C 45/35    (2006.01)
  B01J 8/04    (2006.01)

(52) U.S. Cl. ............ 562/545; 568/476; 422/197

(58) Field of Classification Search ............ None
  See application file for complete search history.

(56) References Cited

U.S. PATENT DOCUMENTS

| | | | |
|---|---|---|---|
| 3,147,084 A * | 9/1964 | Franzen et al. | ............ 422/197 |
| 3,801,634 A * | 4/1974 | Krabetz et al. | ............ 562/532 |
| 3,871,445 A * | 3/1975 | Wanka et al. | ........ 165/104.14 |
| 4,028,070 A | 6/1977 | Uchii et al. | |
| 4,256,783 A * | 3/1981 | Takada et al. | ............ 422/197 |
| 4,837,360 A | 6/1989 | Kadowaki et al. | |
| 5,198,581 A | 3/1993 | Kawajiri et al. | |
| 5,719,318 A | 2/1998 | Kawajiri et al. | |
| 5,739,391 A * | 4/1998 | Ruppel et al. | ............ 562/532 |
| 5,821,390 A | 10/1998 | Ruppel et al. | |
| 6,028,220 A | 2/2000 | Wada et al. | |
| 6,069,271 A * | 5/2000 | Tanimoto et al. | ............ 562/545 |
| 6,179,966 B1 | 1/2001 | Shimizu et al. | |

FOREIGN PATENT DOCUMENTS

| | | | |
|---|---|---|---|
| EP | 0 293 224 A1 | | 11/1988 |
| JP | 11080052 A | * | 3/1999 |
| JP | 2001-19655 A | | 1/2001 |
| JP | 2001129384 A | * | 5/2001 |
| JP | 2001137689 A | * | 5/2001 |
| JP | 2001139499 A | * | 5/2001 |
| KR | 2001-0050268 A | | 6/2001 |
| WO | WO-2004/007064 A1 | | 1/2004 |

* cited by examiner

*Primary Examiner*—Sikarl A. Witherspoon
(74) *Attorney, Agent, or Firm*—Birch, Stewart, Kolasch & Birch, LLP (57) ABSTRACT

The present invention provides a process of producing unsaturated aldehydes and unsaturated acids from olefins by fixed-bed catalytic partial oxidation in a shell-and-tube heat exchanger-type reactor. In this process, the reactor comprises a first-step reaction zone of mainly producing the unsaturated aldehydes, a second-step reaction zone of mainly producing the unsaturated acids, or both the two zones. The first-step reaction zone is divided into two or more zones by a partition. Each of the divided shell spaces is filled with a heat transfer medium, and the heat transfer medium in each shell space is maintained at isothermal temperature or a temperature difference of 0-5° C. The temperatures of the heat transfer media in each of the divided shell spaces are set to increase in the moving direction of reactants. In order to facilitate the removal of heat generation at a location where the partition is placed, a reaction inhibition layer is disposed in the first-step reaction zone. Also, in order to protect the catalyst layer from a highly exothermic reaction, the process is performed at a limited temperature difference between the temperature in a hot spot and the temperature of a molten salt. If the improved heat control system according to the present invention is used, the heat stability of the catalyst layer will be secured and the yields of intermediate and final products can be increased.

16 Claims, 4 Drawing Sheets

METHOD OF PRODUCING UNSATURATED ALDEHYDE AND UNSATURATED ACID IN FIXED-BED CATALYTIC PARTIAL OXIDATION REACTOR WITH ENHANCED HEAT CONTROL SYSTEM

This Non-provisional application claims priority under 35 U.S.C. § 119(a) on Patent Application No(s). 10-2003-0060736 filed in Korea, Republic of on Sep. 1, 2003, the entire contents of which are hereby incorporated by reference.

1. Technical Field

The present invention relates to a process of producing unsaturated aldehydes and unsaturated acids from olefins by catalytic vapor phase oxidation, particularly a process of producing acrolein and acrylic acid from propylene, as well as a heat exchanger-type reactor for use in such a process, particularly a fixed bed shell-and-tube heat exchanger-type reactor. The process of producing unsaturated aldehydes and unsaturated acids corresponds to typical catalytic vapor phase oxidation.

2. Background Art

Generally, catalytic vapor phase oxidation is carried out by charging one or more kinds of granular catalysts into a reactor tube (catalytic tube), supplying feed gas into a reactor through a pipe, and contacting the feed gas with the catalyst in the reactor tube. Reaction heat generated during the reaction is removed by heat exchange with a heat transfer medium whose temperature is maintained at a predetermined temperature. The heat transfer medium for heat exchange is provided on the outer surface of the catalytic tube so as to perform heat transfer. The reaction mixture containing the desired product is collected and recovered through a pipe, and sent to a purification step.

Since the catalytic vapor phase oxidation is a highly exothermic reaction, it is very important to control reaction temperature in a certain range and to reduce the size of the temperature peak at a hot spot occurring in a reaction zone.

It is impossible to satisfactorily control reaction heat from the catalytic vapor phase oxidation only by uniform circulation of the heat transfer medium in the reactor, and the serious temperature peak at the hot spot mentioned above often occurs, causing excessive oxidation at local sites in the reactor. This results in an increase in an undesirable combustion reaction, thus reducing the yield of the desired product. In addition, the catalyst is always locally exposed to high temperature caused by the presence of the hot spot, thus reducing the life cycle of the catalyst.

The partial oxidation of olefin uses a mixture of molybdenum and bismuth or vanadium oxide or mixed oxide thereof, as a catalyst. Typical examples thereof include a process for the production of acrolein or acrylic acid by the oxidation of propylene, a process for the production of phthalic anhydride by the partial oxidation of naphthalene or orthoxylene, and a process for the production of maleic anhydride by the partial oxidation of benzene, butylene or butadiene.

Generally, acrylic acid, a final product, is produced from propylene by a two-step process of vapor phase catalytic partial oxidation. In the first step, propylene is oxidized by oxygen, dilution inert gas, steam and a certain amount of a catalyst, so as to mainly produce acrolein, and in the second step, the produced acrolein is oxidized by oxygen, inert dilution gas, steam and a certain amount of a catalyst, so as to produce acrylic acid. The catalyst used in the first step is a Mo-Bi-based oxidation catalyst which oxidizes propylene to mainly produce acrolein. Also, some acrolein is continuously oxidized on such a catalyst to produce acrylic acid. The catalyst used in the second step is a Mo-V-based oxidation catalyst which oxidizes acrolein, mainly producing acrylic acid.

A reactor for performing such a process is provided either in such a manner that both the two-steps can be performed in one catalytic tube or in such a manner that the two steps can be performed in different catalytic tubes. U.S. Pat. No. 4,256,783 discloses such a reactor.

Meanwhile, acrylic acid manufacturers now conduct diversified efforts either to improve the structure of such a reactor so as to increase the production of acrylic acid by the reactor, or to propose the most suitable catalyst to induce oxidation, or to improve process operations.

In part of such prior efforts, propylene which is supplied into the reactor is used at high space velocity or high concentration. In this case, there are problems in that rapid oxidation in the reactor occurs, making it difficult to control the resulting reaction temperature, and also a high temperature at hot spot in the catalyst layer of the reactor is produced so as to increase reaction temperature, resulting in an increase in the production of byproducts, such as carbon monoxide, carbon dioxide and acetic acid, thus reducing the yield of acrylic acid.

Furthermore, in the case of producing acrylic acid using high space velocity and high concentration of propylene, as the reaction temperature abnormally behaves in the reactor, various problems, such as the loss of active ingredients from the catalyst layer, a reduction in the number of active sites caused by the sintering of metal components, are caused, thus deteriorating the function of the catalyst layer.

Accordingly, in the production of acrylic acid, the control of the heat of reaction in the relevant reactor is important of all things. Particularly, not only the formation of hot spots in the catalytic layer but also the accumulation of heat around the hot spots must be inhibited, and the reactor must be effectively controlled such that the hot spots do not lead to reactor runaway (a state where the reactor is not controlled or explodes by a highly exothermic reaction).

Thus, it is very important to inhibit hot spots and heat accumulation around the hot spots so as to extend the life cycle of a catalyst and inhibit side reactions, thus increasing the yield of product such as acrylic acid. To achieve this inhibition, various attempts have been steadily made.

A fundamental method is to form several catalyst layers having activities that vary according to the moving direction of reactants. Namely, at a reactor inlet side where hot spots generate, a catalytic layer with low activity is formed, and catalyst layers whose activities increase slowly toward a reactor outlet side are formed. Typical methods for controlling catalytic activity include: a method of making catalytic particles by mixing a catalytic material with inactive materials (e.g., U.S. Pat. No. 3,801,634, Japanese patent No. 53-30688B, and Japanese patent No. 63-38831); a method of controlling activity and selectivity by either changing the kind of alkali metals and controlling the amount thereof (e.g., U.S. Pat. No. 4,837,360); a method of controlling activity by adjusting the occupied volume of catalytic particles (e.g., U.S. Pat. Nos. 5,198,581 and 5,719,318); and a method for controlling activity by controlling sintering temperature in the preparation of a catalyst (e.g., U.S. Pat. No. 6,028,220). However, such methods have some effects but still need to be improved.

The method of mixing the catalytic material with the inactive materials is the simplest method to control activity. However, in this method, the filling length of a catalytic layer must be significantly lengthened due to the use of the inactive materials, and uniform mixing of the catalytic particles and the inactive particles acts as excessive load since it requires a significant effort and time.

The method of using alkali metals is a significantly good method since it allows not only the control of activity but also an increase in selectivity. However, since alkali metals in a catalytic composition cause a change in activity and selectivity even at a very low amount, there is a risk in that a small error in the preparation of a catalyst will lead to a great reduction in yield.

Even when significant parts of the above-mentioned problems are solved, in order that the above technologies are more effectively used, a reactor system needs to be designed such that it is suitable for oxidation with excessive heat generation. Particularly, in order to inhibit the inactivation of a catalyst caused by excessive heat generation, it is necessary to establish an efficient heat control system capable of controlling a hot spot and runaway. For the establishment of the efficient heat control system, studies have been performed on the introduction of a perforated shield plate (e.g., U.S. Pat. No. 4,256,783, European patent No. 293224A, and Japanese patent No. 52-83936), the establishment of circulation pathway of molten salts by the placement of various baffles (e.g., U.S. Pat. No. 3,871,445), the design of an oxidation reactor integrated with a cooling heat exchanger (e.g., U.S. Pat. No. 3,147,084), a multi-stage heat control structure using an improved heat exchanger system (e.g., Korean patent application No. 10-2002-40043, and PCT/KR02/02074), etc.

As described above, since the catalytic vapor phase oxidation is an exothermic reaction which not only progresses at high temperature but also has excessive heat generation, it can cause a reduction in selectivity due to the generation of a hot spot with very high temperature around a reactor inlet or the accumulation of heat around the heat spot, and also can result in a significant reduction in the performance of a catalyst in a long-term viewpoint. Particularly, if the temperature of the hot spot is higher than the calcination temperature of the catalyst, the life cycle of the catalyst will be reduced to shorten the replacement time of the entire catalyst layers, resulting in an economical loss. In addition, if the activity of the filled catalyst layers is reduced and the temperature of a heat transfer medium (molten salt) is elevated in order to compensate for the reduction in activity, the temperature of a hot spot and the accumulation of heat in the hot spot will also be increased, and as a result, a solution to solve this problem is required.

DISCLOSURE OF THE INVENTION

In view of the above-mentioned problems occurring the prior art, the present inventors have made improvements in a fixed-bed shell-and-tube heat exchanger-type reactor of producing unsaturated aldehydes and unsaturated acids from olefins either using a single reactor where two-step reaction is conducted or using two reactors which are connected in series with each other. In the improvements, the first-step reaction zone of the reactor was divided into two or more zones in an axial direction by a partition, and the temperature of a heat transfer medium filled in each of the divided shell spaces of the first-step reaction zone was independently set to a temperature suitable for the activity of a catalyst and the degree of reaction. As a result of such improvements, the present inventors have found that a hot spot and heat accumulation around the hot spot could be inhibited. The present invention was perfected based on this finding.

An object of the present invention is to provide a production process in which the temperature difference between the peak temperature of a catalyst layer in each of the divided reaction zone and the temperature of a heat transfer medium (molten salt) filled in the shell space corresponding to that zone is controlled, so that the process is not only thermally stable but also can be operated without a reduction in yield, even in the presence of a catalyst with very high activity, as well as an improved heat exchange-type reactor for use in this process.

Another object of the present invention is to provide a production process in which a reaction inhibition layer is inserted in order to facilitate the removal of heat generation at a location where the partition is placed, as well as a shell-and-tube heat exchanger-type reactor for use in this process.

In one aspect, the present invention provides a process of producing unsaturated aldehydes and unsaturated acids from olefins, particularly a process of producing acrolein and acrylic acid from propylene, by fixed-bed catalytic partial oxidation in a shell-and-tube heat exchanger-type reactor, the reactor comprising one or more catalytic tubes each including a first-step reaction zone of mainly producing the unsaturated aldehydes, a second-step reaction zone of mainly producing the unsaturated acids, or both the two zones, the improvement wherein: the first-step reaction zone is divided into two or more zones by a partition, each of the divided shell spaces being filled with a heat transfer medium, the heat transfer medium being maintained at isothermal temperature or a temperature difference of 0–5° C., in which the temperatures of the heat transfer medium in each of the divided shell spaces are set to increase in the moving direction of reactants, and/or a difference between the temperature of the heat transfer medium and the temperature of a hot spot is limited, and/or a reaction inhibition layer is inserted into a location where the partition is placed.

In another aspect, the present invention provides a shell-and-tube heat exchanger-type reactor which can be used in a process of producing unsaturated aldehydes and unsaturated acids from olefins by fixed-bed catalytic partial oxidation, the reactor comprising one or more catalytic tubes each including a first-step reaction zone of mainly producing the unsaturated aldehydes, a second-step reaction zone of mainly producing the unsaturated acids, or both the two zones, the improvement wherein the first-step reaction zone is divided into more than two zones by a partition, each of the divided shell spaces being filled with a heat transfer medium, the heat transfer medium being maintained at isothermal temperature or at a temperature difference of 0–5° C., in which the temperatures of the heat transfer medium in each of the divided shell spaces are set to increase in the moving direction of reactants, and/or a difference between the temperature of the heat transfer medium and the temperature of a hot spot is limited, and/or a reaction inhibition layer is inserted into a location where the partition is disposed.

As used herein, the term "each of the shell spaces" indicates an internal space surrounded by a catalytic tube, a shell, a partition, a tube sheet, etc.

As described below, the present invention makes improvements in the first-step reaction region of mainly producing unsaturated aldehydes and unsaturated acids, and aims to use an improved heat control system to inhibit a hot spot and heat accumulation at the hot spot and to increase the yield in an intermediate step, and at the same time, to make stable the reaction in the second-step reaction zone while increasing final yield.

In the inventive production process and heat exchanger-type reactor, the temperature of the heat transfer medium in each of the divided shell spaces is set as nearly as possible to isothermal conditions. According to the amount of heat generation and the capacity of the heat transfer medium, the temperature difference between portions of the heat transfer medium, which correspond to both the ends of a catalyst layer in each of the divided shell spaces, is preferably 0–5° C., and more preferably 0–3° C.

Examples of the heat transfer medium include very highly viscous media, for example a molten salt which consists mainly of a mixture of potassium nitrate and sodium nitrite. Other examples of the heat transfer medium include phenyl ether media (e.g., "Dowtherm"), polyphenyl media (e.g., "Therm S"), hot oil, naphthalene derivatives (S.K. oil) and mercury.

By controlling the flow rate of the heat transfer medium, the reaction throughout the tube corresponding to each of the shell spaces in the reactor can be carried out at substantially the same temperature of the heat transfer medium.

The temperature of the heat transfer media in the adjacent shell spaces in each of the reaction zones is preferably set to increase in an axial direction by a temperature difference of 0–50° C., and more preferably 5–15° C.

As the temperature of the heat transfer medium filled in each of the shell spaces increase in the moving direction (hereafter, referred to as "axial direction") of reactants, the reactivity of the catalyst layer increases in the axial direction.

If the temperature of the heat transfer medium in each of the shell spaces divided by the partition increases in the axial direction, a hot spot and heat accumulation around the hot spot can be inhibited.

Since a reactor front portion with high reactant concentration and high reaction pressure has the highest reactivity, a hot spot with significantly high temperature is formed in the reactor front portion. If the temperature of the heat transfer medium in a portion of the shell space, which corresponds to a location where this hot spot is formed, is decreased to the lowest possible active temperature, the size of the hot spot can be reduced and heat accumulation around the hot spot can be prevented while causing no significant reduction in reactivity.

In the case of inducing a continuous increase in temperature without the partition, excessive efforts are required in order to remove reaction heat caused by catalytic oxidation or to inhibit heat accumulation, and it is very difficult to exactly set the desired temperature profile.

The location of the partition is preferably established based on the exact prediction of a position where a hot spot is formed.

A hot spot is produced by the generation of reaction heat resulting from catalytic vapor phase oxidation, and determined by the composition of reactants, the flow rate (L/min) of reactants, the temperature of a heat transfer medium, etc., and has a certain position and size in a certain process condition. However, the activity of a catalyst can change with time.

In portions where heat control is problematic, a hot spot can be generated in the front portion of a first-step oxidation catalyst layer, in which olefin (propylene), a main reactant, and molecular oxygen, are present at high concentrations. Also, if two or more catalyst layers are used in the first-step oxidation zone, a hot spot can be generated around the boundary between the adjacent catalyst layers.

The partition is preferably located at either a position where a hot spot or heat accumulation resulting from the hot spot are problematic, or a position allowing the largest possible removal of heat generation in each zone.

A hot spot is the site of the maximum temperature peak, and each of catalyst layers generally has at least one hot spot.

Also, it is preferred that the temperature of the heat transfer medium (molten salt or heat transfer salt) in each of the divided shell spaces is set in such a manner that a catalyst has optimal activity.

Particularly in the present invention, in order to inhibit a hot spot and heat accumulation resulting from the hot spot either in a catalytic tube for each reaction step or in each reaction zone in one catalytic tube under high olefin concentration or high olefin space velocity, the temperature of the heat transfer medium is changed in the axial direction so as to reduce catalyst damage caused by a highly exothermic reaction and to inhibit a reduction in yield caused by side reactions, resulting in an increase in yield.

The present invention provides a production process and reactor, wherein, when the shell spaces divided by the partition in the first-step reaction zone are named, such as zone 1, zone 2, zone 3, . . . in the axial direction, $T_{h1}-T_{salt1}$ is $\leq 150°$ C., and preferably $T_{h1}-T_{salt1}$ is $\leq 110°$ C., and $T_{hN}-T_{saltN}$ is $\leq 120°$ C., and more preferably $T_{hN}-T_{saltN}$ is $\leq 100°$ C. where N is an integer of 2 or more.

Here, $T_{h1}$ is the peak temperature of a reaction mixture in a catalyst layer corresponding to the first shell space (the peak temperature of the catalyst layer), and $T_{hN}$ is the peak temperature of a reaction mixture in a catalyst layer corresponding to the Nth shell space. And $T_{salt1}$ is the temperature of a heat transfer medium (molten salt) filled in the first shell space, and $T_{saltN}$ is the temperature of a heat transfer medium filled in the Nth shell space.

In the first shell space, the concentration and pressure of reactants are high, so that the temperature difference between the peak temperature of the catalyst layer and the temperature of the molten salt is higher than that in the next shell space. For this reason, the temperature difference range in the first shell space will be surely wider than those in the next shell spaces. However, the present invention provides a method by which the magnitude of peak temperature in the first shell space is minimized while a temperature difference in the next shell space is also limited to a certain range, so as to prevent local excessive heat generation, thus making smooth the shape of temperature profile, in which the limited temperature range is the result of various experiments conducted over several years by the present inventors. If operations are done without such a limited range, the sintering of a catalyst in a hot spot, the loss of important metal components, an increase in byproducts, etc., can be caused, and particularly accidents can also occur due to a sudden exothermic reaction when introducing raw materials into a reactor. For these reasons, the inventive method is technologically necessary for safe start-ups, stable operations, and safe shut-downs.

According to the present invention, the temperature difference between the peak temperature of a catalyst layer in each reaction zone and the temperature of a heat transfer medium (molten salt) is controlled in the above-specified range, so that the catalyst can show uniform activity in the axial direction, and the degree of reaction can be suitably controlled, so as to inhibit heat accumulation in a hot spot and suppress side reactions, thus preventing a reduction in yield.

Accordingly, the present invention can be stably operated at high olefin concentration or high space velocity without the control of activity of a catalyst filled in the first-step reactor. Meanwhile, in the production of unsaturated aldehydes and unsaturated acids from olefins, the olefins can be introduced into a reactor inlet at a space velocity of 50–130 $hr^{-1}$.

The method of filling a plurality of catalyst layers with varying activities in the first-step reaction zone can achieve better performance by reducing the magnitude of peak temperature at a hot spot and inhibiting heat accumulation. However, in such a method, there is a shortcoming in that different kinds of catalysts must be prepared and filled separately, thus causing the problem of an increase in catalyst costs. Furthermore, since it is very difficult to control not only the size and shape of a catalyst corresponding to each of the catalyst layers but also the content of alkali metals and alkaline earth metals, it is a great load to prepare various kinds of catalysts in such a manner that the catalysts have uniform performances every time. On the other hand, in the present invention, a multi-step heat control system is applied even in the catalyst layers with the same activity, so that a process and reactor of producing acrolein and acrylic acid in an efficient and stable manner can be provided.

According to one embodiment of the present invention, improvements are made in a process of producing acrolein and acrylic acid by reacting propylene with molecular oxygen, dilute inert gas and steam under a catalyst, optionally with recycled off-gas which had not been absorbed into an absorbing column. In the improvements, the first-step reaction step of producing acrolein and acrylic acid is divided into two or more separate shell spaces in an axial direction, and the temperature of a heat transfer medium filled in each of the shell spaces is set to increase in the axial direction, so that the reactivity of the catalyst layers increases in the axial direction.

In the first-step reaction zone where acrolein is mainly produced from propylene, the temperature of the catalyst layer with activity is set to about 290–420° C. and the temperature of the heat transfer medium is set to about 290–350° C. In this reaction zone, acrylic acid, carbon monoxide, carbon dioxide, steam, acetic acid and small amounts of byproducts are produced in addition to acrolein. Since the oxidation in this step is a reaction which progresses at high temperature and is highly exothermic, heat of 81 kcal per g-mol of propylene occurs and the temperature in a hot spot reaches 370–400° C. In the second-step reaction zone where acrylic acid is mainly produced from acrolein, the temperature of the catalyst layer with activity is set to about 260–360° C. and the temperature of the heat transfer medium is set to about 260–330° C. In this second reaction zone, unreacted acrolein, carbon monoxide, carbon dioxide, steam, acetic acid, unreacted propylene and small amounts of byproducts are produced in addition to acrylic acid. Since the second-step reaction is also a reaction which progresses at high temperature and is highly exothermic, heat of 60 kcal per g-mol of acrolein occurs and the temperature in a hot spot reaches 310–350° C.

In the structure of the reactor according to the present invention, the first-step reaction zone is divided into two or more shell spaces by a partition such that the temperature of a heat transfer medium filled in each of the divided shell spaces can be controlled independently. The temperature of the heat transfer medium filled in each shell space is set to increase in an axial direction. For example, if the shell space corresponding to the first-step reaction region is divided into three separate spaces, two partitions will be vertically disposed to an axis of catalytic tube inside the shell space to provide a structure with three shell spaces in which the temperature of the heat transfer medium is controlled independently. The heat transfer mediums filled in the spaces are set to increasing temperatures of, for example, 300° C., 310° C. and 315° C., respectively, in an axial direction from the reactor inlet to the outlet.

Meanwhile, the catalyst layer in the first-step reaction zone may consist of one layer with axially uniform activity, or if necessary, two or more stacked layers with increasing activity toward the outlet. The catalyst layer in the second-step reaction zone may consist of one layer with axially uniform activity, or if necessary, two or more stacked layers with increasing activity toward the outlet.

The number of catalytic tubes in a commercial shell-and-tube reactor of producing acrylic acid reaches several thousands to several tens of thousands, and a partition disposed in the reactor has a very large thickness of 50–100 mm. Thus, if the shell space in each of the two-step reaction zones is divided into two or more layers, the removal of heat generation due to reaction in a position where a partition is disposed is not easy, thus causing a problem in heat transfer. To eliminate such a problem, the present invention is also characterized by providing a layer made of an inactive material alone or a mixture of an inactive material and a catalytic material, i.e., a reaction inhibition layer, within a portion of the catalytic tube, which corresponds to a position where the partition is disposed.

Such a reaction inhibition layer is a layer with different characters from an inactive layer which is filled between the first step (propylene to acrolein) and second reaction step (acrolein to acrylic acid) to a thickness of about 400–1,000 mm so as to induce cooling to a reaction temperature suitable for the second-step reaction. This reaction inhibition layer is a filling layer for minimizing heat generation in a position where heat transfer is problematic. The volume ratio of an inactive material to a catalytic material in this reaction inhibition layer is 20–100%, and preferably 80–100%. The filling height of the reaction inhibition layer is 20–500%, and preferably 120–150% of the thickness of the partition, indicating that the reaction inhibition layer completely overlaps the thickness of the partition. However, if the height of the reaction inhibition layer must be made smaller than the thickness of the partition, it is preferably filled in such a manner that the largest possible area overlaps.

The inactive material used in the reaction inhibition layer is designated as a material which is inactive to a reaction of producing unsaturated aldehydes and unsaturated acids from olefins, for example, a catalytic oxidation of producing acrolein and acrylic acid from propylene. It can be used in a sphere, cylinder, ring, rod, plate or wire mesh shape, or a mass shape with suitable size, or a suitable combination thereof. Widely known examples of the inactive material include alumina, silica, stainless steel, iron, steatite, porcelain, various ceramics, and mixtures thereof.

The catalytic tube in the reactor may comprise one or more catalyst particle layers for each oxidation step.

BEST MODE FOR CARRYING OUT THE INVENTION

Hereinafter, the present invention will be described in detail with reference to the accompanying drawings. FIGS. 1 to 4 show a pilot structure designed to transfer the idea of the present invention, and the scope of the present invention is not limited only to details shown in the drawings.

It is known that reactor behavior characteristics, such as temperature, yield, etc, in an actual shell-and-tube heat exchanger-type reactor, can be represented by a reactor with one catalytic tube. Thus, the effects of the present invention will be proven by a pilot experiment with one catalytic tube for each reaction step.

Figure 1:
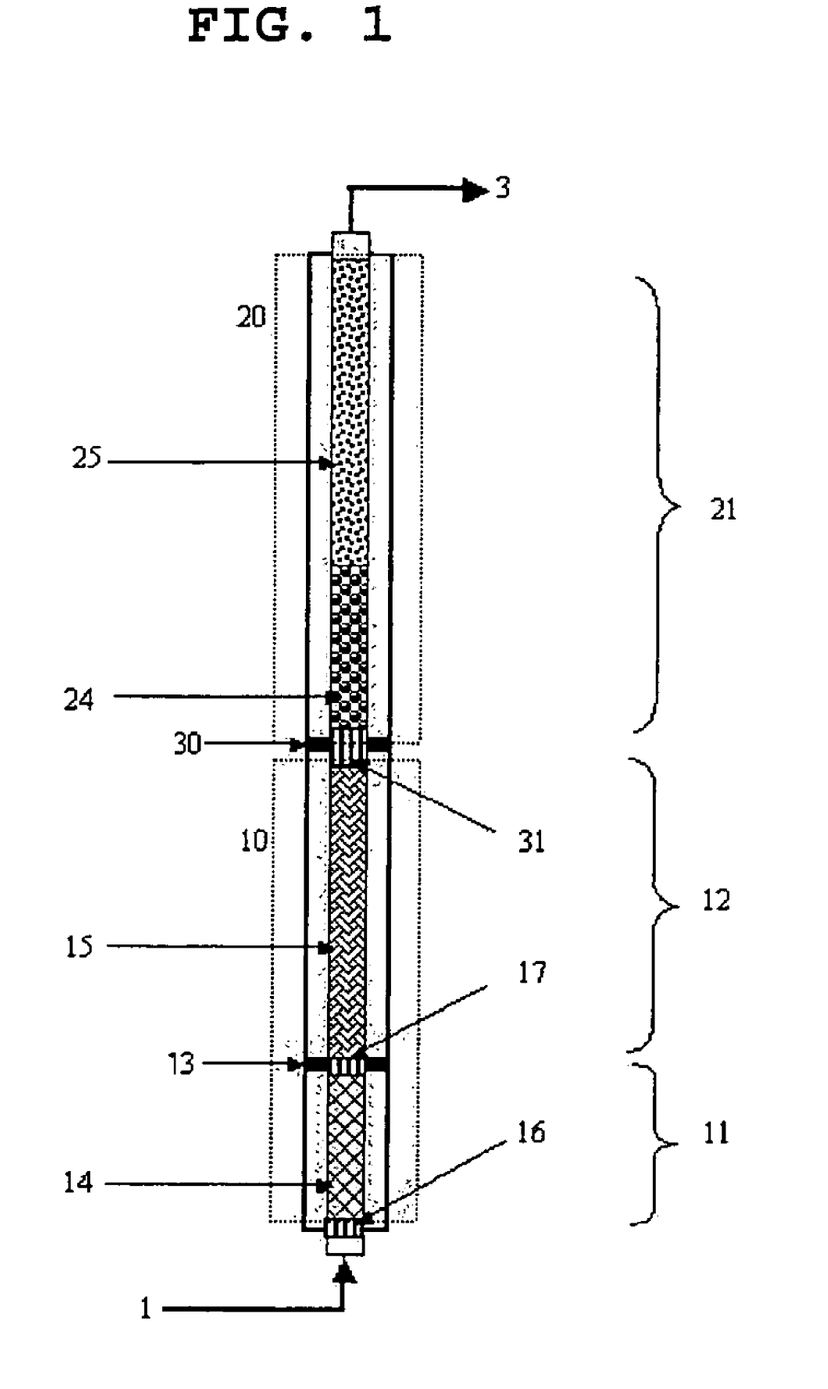
FIG. 1 is a schematic diagram showing the structure of a catalyst layer in a pilot reactor in which first-step reaction and second-step reaction are successively performed in one catalytic tube.

For the description below, a catalyst layer for each step is named as follows, and the following sequence coincides with a reaction pathway:

The first catalyst layer in the first-step reaction: a first step-layer A;

The second catalyst layer in the first-step reaction: a first step-layer B;

The third catalyst layer in the first-step reaction: a first step-layer C;

The first catalyst layer in the second-step reaction: a second step-layer A;

The second catalyst layer in the second-step reaction: a second step-layer B;

The third catalyst layer in the second-step reaction: a second step-layer C;

If necessary, the catalyst layers may be disposed in such a manner that their catalytic activity gradually increases toward the layers A, B, C, FIG. 1 shows the structure of a pilot reactor in which two-step reaction occurs in one catalytic tube. As shown in FIG. 1, a first-step reaction zone 10 and a second-step reaction zone 20 are connected in series with each other, such that reactants fed into a reactor inlet are subjected to first-step reaction and then to second-step reaction, thus producing acrylic acid. If necessary, two or more catalyst layers with different activities (except for an inactive material layer and a reaction inhibition layer) can be included in each of the reaction zones.

Hereinafter, a detailed description on a reaction system based on two catalyst layers with different activities for each reaction step will be made by way of an example.

Reference numerals 11, 12 and 21 in FIG. 1 denote shell spaces (jackets) into which heat transfer media with different temperatures are filled. FIG. 1 shows the structure of the catalyst layers in the catalytic tube, and the following layers are filled in the catalytic tube in an order from the lower level to the upper level:

Inactive particle-layer A 16
First-step reaction zone:
First step-layer A 14
First step-reaction inhibition layer 17
First step-layer B 15
Inactive particle-layer B 31
Second-step reaction zone:
Second step-layer A 24
Second step-layer B 25

The first step-layer A and the first step-layer B can be catalyst layers with the same or different activities. The second step-layer A and the second step-layer B can be catalyst layers with the same or different activities. Between the first-step reaction zone and the second-step reaction zone, inactive particles (inactive particle-layer B) are suitably filled such that the temperature of a reaction mixture entering the second step is in the range of activation temperature of second step-layer A. The shell space in the first-step reactor is divided into two heat control spaces which are heat-controlled independently. As shown in FIG. 1, a partition 13 in the first-step reaction zone is located at a boundary between the catalyst layers. Reference numeral 30 in FIG. 1 denotes a partition of providing a division between the first-step and second-step reaction zones, and the inactive material layer 31 is a filling layer of inducing reactants to be cooled to a temperature suitable for the catalyst layer 24 in the second-step reaction zone.

Reference numeral 1 in FIG. 1 denotes the flow of reactants consisting of propylene, molecular oxygen, dilute gas, and steam. Reference numeral 3 denotes the flow of products consisting of main product acrylic acid, dilute gas, molecular oxygen, unreacted propylene, unreacted acrolein, and small amounts of byproducts, etc.

Reference numerals 11 and 12 in FIG. 1 denote two divided shell spaces (jackets) in the first-step reaction zone, and reference numeral 21 in FIG. 1 denotes a shell space (jacket) in the second-step reaction zone.

Figure 2:
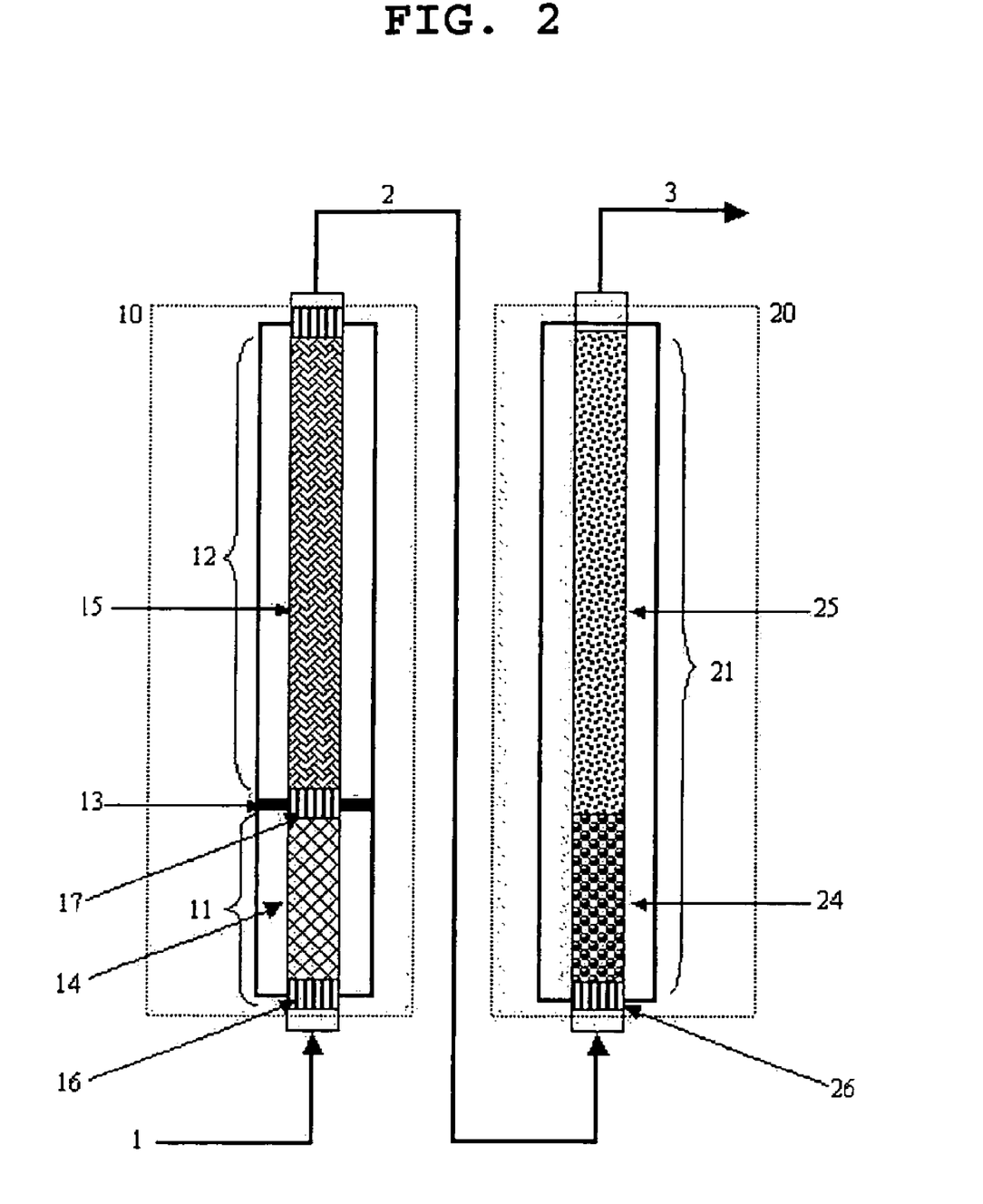
FIG. 2 is a schematic diagram showing the structure of a pilot reactor consisting of two catalytic tubes, and the structure of a catalyst layer in each of the catalytic tubes. First-step reaction and second-step reaction is conducted in the two catalytic tubes, respectively, and a partition is placed at a boundary between the catalyst layers in first-step reactor.

FIG. 2 shows the structure of a pilot reactor in which a first-step reaction zone and a second-step reaction zone are divided from each other. In FIG. 2, the fundamental structure of the reactor, and the structure of the catalyst layer, are the same as those in FIG. 1.

Figure 3:
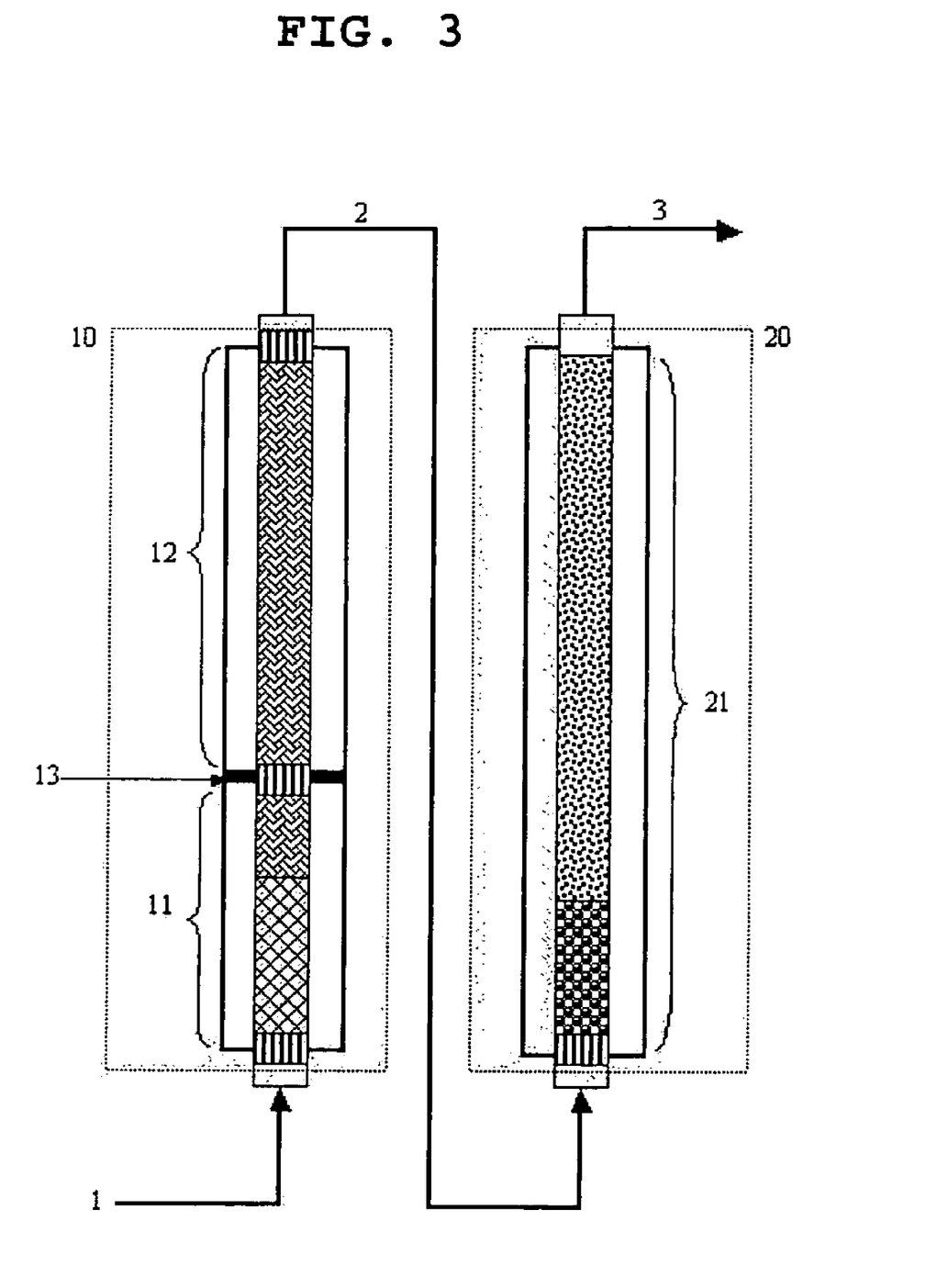
FIG. 3 is a schematic diagram showing the structure of a pilot reactor consisting of two catalytic tubes, and the structure of a catalyst layer in each of the catalytic tubes. First-step reaction and second-step reaction is conducted in the two catalytic tubes, respectively, and a partition is not placed at a boundary between the catalyst layers in first-step reactor.
Figure 4:
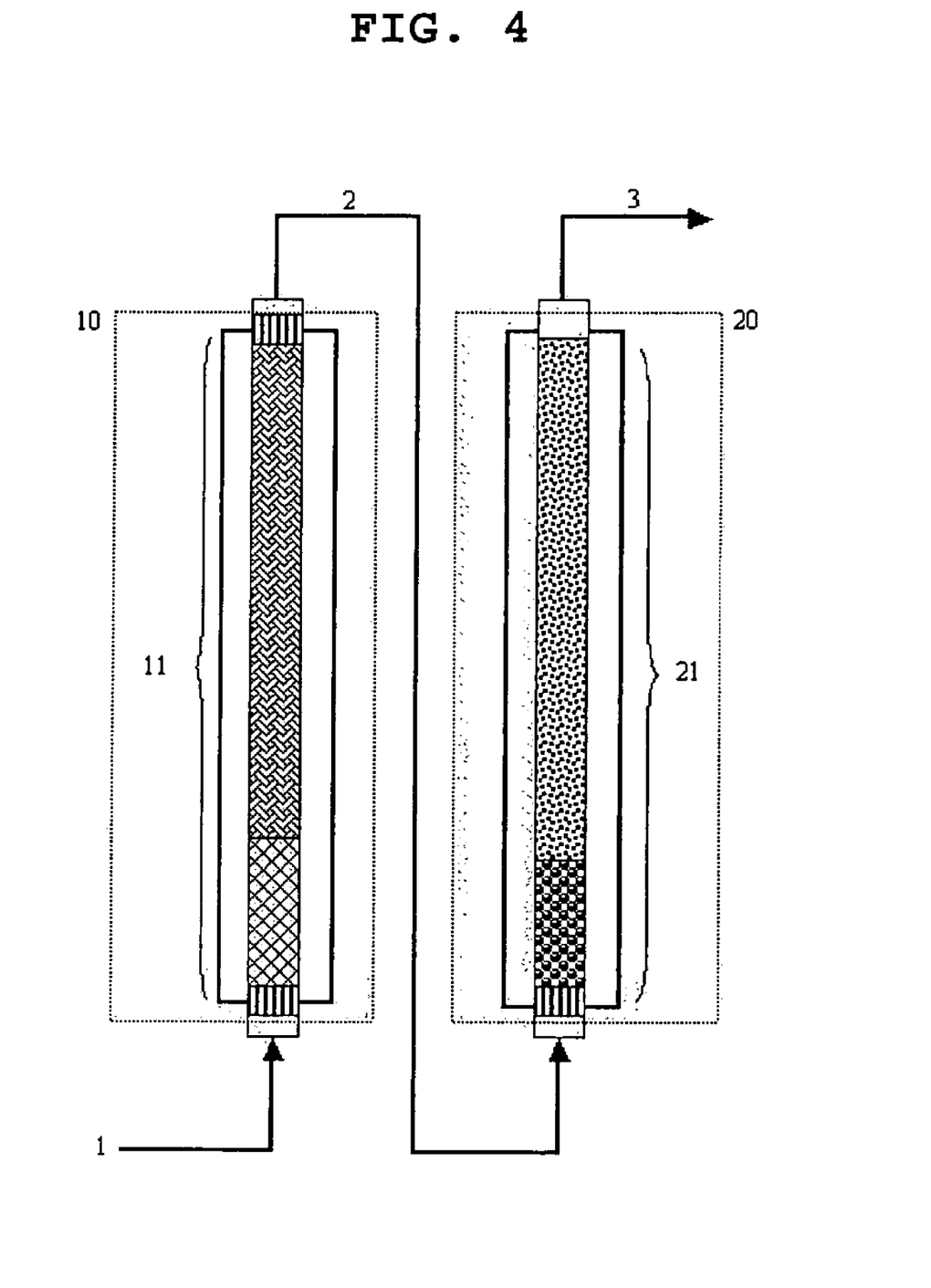
FIG. 4 is a schematic diagram showing the structure of a pilot reactor consisting of two catalytic tubes, and the structure of a catalyst layer in each of the catalytic tubes. First-step reaction and second-step reaction is conducted in the two catalytic tubes, respectively, and a partition is not disposed in the pilot reactor.

FIG. 3 shows a structure where two or more catalyst layers with different activities are filled in each of the reaction zones. In this structure, a partition is placed away from a boundary between the catalyst layers. Also, this structure can be used when first heat control zone is defined by a section ranging from a reactor inlet to the peak temperature zone of the first step-layer B, and the second heat control zone is defined by the remaining section. Also, this structure can be applied when two or more adjacent temperature peaks are present in the catalyst layer so that such temperature peaks need to be controlled at the same time using one shell space (jacket).

For example, peak temperatures occurring in the first step-layer A and the first step-layer B can be controlled below a pre-determined peak temperature of catalyst layers to be managed, by controlling the temperature of a heat transfer medium filled in the first heat control zone. In FIG. 3, a method of positioning the partition, and a method of filling the catalyst and the inactive material, can also be applied to the reactor structure with one catalytic tube as shown in FIG. 1, in the same principle.

In the location of the partition in the catalyst layer, the partition can be disposed between the preceding catalyst layer and the relevant catalyst layer in the filling order, and a second partition can be disposed following the peak position of the relevant catalyst layer. If the relevant catalyst layer is a first catalyst layer either at a reactor inlet or at the initiation point of each of the reaction zones, one partition will be disposed following the peak point of the relevant catalyst layer. The shell spaces divided by the partition may cover the position of one or more peak temperatures occurring in a plurality of the catalyst layers.

The inventive heat control system can be applied in the oxidation of olefins, and also in a reaction system where the kind of reaction varies in an axial direction so that it progresses for each step, as well as a system where reaction temperature must be changed according to reaction zones so that it is controlled at the optimal temperature.

EXAMPLE 1

Improved Heat Control System): Changes in Yield and the Magnitudes of Temperature Peaks at Hot Spots with Change in Setting Temperature of Molten Salt As shown in FIG. 3, a pilot reactor was provided in which each of first-step reaction and second-step reactions is conducted in one catalytic tube (included in the zone 10 or 20 of FIG. 3). Each of the catalytic tubes is 26 mm in inner diameter, and the first-step catalytic tube was filled with catalytic layers with a height of about 1200 mm, and the second-step catalytic tube was filled with catalytic layers with a height of about 1100 mm. Reference numerals 11 and 12 in FIG. 3 denote the divided shell spaces of the first-step reaction zone. The temperatures of molten salts filled in the shell spaces are 300° C. and 305° C., respectively. Reference numeral 21 in FIG. 3 is a shell space into which a molten salt is filled and set to 265° C. The two catalyst layers filled in the first-step reaction zone 10 are made of a catalyst based on molybdenum (Mo) and bismuth (Bi), the preparation of which is described in Korean patent No. 0349602 (Application No. 10-1997-0045132). The two catalyst layers filled in the second-step reaction zone 20 are made of a catalyst based on molybdenum and vanadium (V), the preparation of which is described in Korean patent No. 0204728 or Korean patent No. 0204729.

The catalytic tube for each reaction step was filled with two catalyst layers whose activity gradually increases from an inlet to an outlet, according to a method for controlling catalytic activity as disclosed in U.S. Pat. Nos. 3,801,634 and 4,837,360.

The catalytic tube in the first-step reaction zone was filled with two catalyst layers having 320 mm and 880 mm, respectively, in an axial direction, and the catalytic tube in the second-step reaction zone were filled with two catalyst layers having 290 mm and 820 mm, respectively, in an axial direction. A partition was disposed at the 600-mm position of the first-step reaction zone, such that it covered both temperature peaks occurring in the two catalyst layers. In a portion inside the catalytic tube corresponding to the position of the partition, an inactive material layer was filled to a thickness corresponding 120% of the thickness of the partition. A pipe inducing a flow represented by reference numeral 2 in FIG. 3 serves to connect the two catalytic tubes and is surrounded by an insulation material. Starting material comprising propylene, steam, oxygen and inert gas enter the reactor through a line 1, passes through the reaction steps, and then flows out from the reactor through a line 3. The starting materials consist of propylene, oxygen, steam and nitrogen gas, in which the amount of propylene is 7% and the ratio of oxygen and propylene is about 1.80. Space velocity is 1400 $hr^{-1}$ (STP) in the first-step reaction zone, and space velocity is 1530 $hr^{-1}$ (STP) in the second-step reaction zone. Also, the space velocity of olefin entering the first-step reaction zone is 98 $hr^{-1}$ (STP).

In the zone corresponding to the first shell space in the first-step reaction zone, a hot spot with a temperature of 381.6° C. was formed. The yields of acrolein and acrylic acid were 81.17% and 8.84%, respectively. In the second-step reaction zone which is operated at isothermal conditions, the temperature of a hot spot was 327° C., and the yields of acrolein and acrylic acid were 0.553% and 84.01%, respectively.

Since a reaction in a reaction inhibition layer (inactive material layer) did not occur, an abnormal increase in temperature was not observed by a reduction in heat transfer efficiency.

EXAMPLE 2

Improved Heat Control System): Changes in Yield and the Magnitudes of Temperature Peaks at Hot Spots with Change in Setting Temperature of Molten Salt This example was performed in the same manner as in Example 1 except for the setting temperatures of a molten salt in the first-step reaction zone (first-step reactor). The temperatures of the molten salt in the first-step reaction zone were set to 300° C. and 310° C., respectively, in an axial direction.

In the zone corresponding to the first shell space in the first-step reaction zone, a hot spot with a temperature of 381.5° C. was formed. The yields of acrolein and acrylic acid were 81.13% and 9.30%, respectively. In the second-step reaction zone which is operated at isothermal conditions, the temperature of a hot spot was 320.0° C., and the yields of acrolein and acrylic acid were 1.18% and 84.35%, respectively.

EXAMPLE 3

Improved Heat Control System): Changes in Yield and the Magnitudes of Temperature Peaks at Hot Spots with Change in Setting Temperature of Molten Salt This example was performed in the same manner as in Example 1 except for the setting temperatures of a molten salt in the first-step reaction zone (first-step reactor). The temperatures of the molten salt in the first-step reaction zone were set to 300° C. and 315° C., respectively, in an axial direction.

In the zone corresponding to the first shell space in the first-step reaction zone, a hot spot with a temperature of 381.2° C. was formed. The yields of acrolein and acrylic acid were 79.02% and 11.46%, respectively. In the second-step reaction zone which is operated at isothermal conditions, the temperature of a hot spot was 327.5° C., and the yields of acrolein and acrylic acid were 0.607% and 84.95%, respectively.

EXAMPLE 4

Improved Heat Control System: Changes in Yield and Magnitudes of Temperature Peaks at Hot Spots with Change in Setting Temperature of Molten Salt This example was performed in the same manner as in Example 1 except for the setting temperatures of a molten salt in the first-step reaction zone (first-step reactor). The temperatures of the molten salt in the first-step reaction zone were set to 300° C. and 320° C., respectively, in an axial direction.

In a zone corresponding to the first shell space in the first-step reaction zone, a hot spot with a temperature of 381.2° C. was formed. The yields of acrolein and acrylic acid were 78.97% and 11.45%, respectively. In the second-step reaction zone which is operated at isothermal conditions, the temperature of a hot spot was 327.0° C., and the yields of acrolein and acrylic acid were 0.607% and 84.88%, respectively.

EXAMPLE 5

Improved Heat Control System: Changes in Yield and Magnitudes of Temperature Peaks at Hot Spots with Change in Setting Temperature of Molten Salt This example was performed in the same manner as in Example 1 except for the setting temperatures of a molten salt in the first-step reaction zone (first-step reactor). The temperatures of the molten salt in the first-step reaction zone were set to 308° C. and 315° C., respectively, in an axial direction.

In a zone corresponding to the first shell space in the first-step reaction zone, a hot spot with a temperature of 392.5° C. was formed. The yields of acrolein and acrylic acid were 80.33% and 11.37%, respectively. In the second-step reaction zone which is operated at isothermal conditions, the temperature of a hot spot was 320.5° C., and the yields of acrolein and acrylic acid were 0.631% and 86.83%, respectively.

EXAMPLE 6

A Case Where Each of Reaction Zones is Filled with Catalysts Having the Same Activity and a Multi-step Heat Control System is Applied Of two catalysts used in the first-step reaction zone in Example 1, a catalyst with higher activity was filled in the first-step reaction zone with a height of 1200 mm. Also, of two catalysts used in the second-step reaction zone in Example 1, a catalyst with higher activity was filled in the second-step reaction zone with a height of 1100 mm. Example 6 was performed in the same manner as in Example 1 except for the structure of the catalyst layer filled in each reaction zone, and the setting temperature of a molten salt. The temperatures of molten salts in two shell spaces corresponding to the first-step reaction zone were set to 295° C. (a shell space corresponding to the first zone) and 305° C. (a shell space corresponding to the second zone). The temperature of molten salts in the second-step reaction zone was set to an isothermal temperature of 265° C.

In the first-step reaction zone which is operated at isothermal conditions, the temperature of a hot spot in the first zone was 392.3° C., and the temperature of a hot spot in the second zone was 363.6° C. The yields of acrolein and acrylic acid were 79.23% and 11.08%, respectively. In the second-step reaction zone which is operated at isothermal conditions, the yields of acrolein and acrylic acid were 0.704% and 85.54%, respectively.

$T_{h1}-T_{salt1}$ was 97.3° C., and $T_{h2}-T_{salt2}$ was 58.6° C.

COMPARATIVE EXAMPLE 1

The Case of Operations Under Isothermal Conditions Without the Application of a Multi-step Heat Control System: Changes in Hot Spot Temperature and Yield with Change in Setting Temperature of Molten Salt Comparative Example 1 was performed in the same manner as in Example 1 except for the setting temperature of molten salts in the first-step reaction zone (first-step reactor) (see FIG. 4). The temperature of the molten salts in the first-step reaction zone was set to an isothermal temperature of 300° C., and no partition was disposed. The temperature of molten salts in the second-step reaction zone was set to an isothermal temperature of 265° C.

In the first-step reaction zone which is operated at isothermal conditions, the temperature of a hot spot was 383.8° C., and the yields of acrolein and acrylic acid were 81.3% and 8.18%, respectively. In the second-step reaction zone which is operated at isothermal conditions, the temperature of a hot spot was 320.1° C., and the yields of acrolein and acrylic acid were 1.583% and 83.11%, respectively.

COMPARATIVE EXAMPLE 2

The Case of Operations Under Isothermal Conditions Without the Application of a Multi-step Heat Control System Changes in Hot Spot Temperature and Yield with Change in Setting Temperature of Molten Salt Comparative Example 2 was performed in the same manner as in Comparative Example 1 except for the setting temperature of molten salts in the first-step reaction zone (first-step reactor). The temperature of the molten salts in the first-step reaction zone was set to an isothermal temperature of 305° C.

In the first-step reaction zone which is operated at isothermal conditions, the temperature of a hot spot was 394.6° C., and the yields of acrolein and acrylic acid were 81.91% and 8.35%, respectively. In the second-step reaction zone which is operated at isothermal conditions, the temperature of a hot spot was 320.3° C., and the yields of acrolein and acrylic acid were 1.424% and 84.07%, respectively.

COMPARATIVE EXAMPLE 3

The Case of Operations Under Isothermal Conditions Without the Application of a Multi-step Heat Control System: Changes in Hot Spot Temperature and Yield with Change in Setting Temperature of Molten Salt Comparative Example 3 was performed in the same manner as in Comparative Example 1 except for the setting temperature of molten salts in the first-step reaction zone (first-step reactor). The temperature of the molten salts in the first-step reaction zone was set to an isothermal temperature of 310° C.

In the first-step reaction zone which is operated at isothermal conditions, the temperature of a hot spot was 405.7° C., and the yields of acrolein and acrylic acid were 80.43% and 10.11%, respectively. In the second-step reaction zone which is operated at isothermal conditions, the temperature of a hot spot was 316.0° C., and the yields of acrolein and acrylic acid were 1.257% and 84.66%, respectively.

COMPARATIVE EXAMPLE 4

A Case Where Each of Reaction Zones is Filled with Catalysts Having the Same Activity: Changes in Hot Spot Temperature and Yield with Change in Setting Temperature of Molten Salt The first-step reaction zone was filled with the catalyst used in Example 6 to a height of 1200 mm. Also, the second-step reaction zone was filled with the catalyst used in Example 6 to a height of 1100 mm. Comparative Example 4 was performed in the same manner as in Example 6 except for the setting temperature of molten salts in each of the reaction zones. The temperature of molten salts in the first-step reaction zone was set to 300° C., and the temperature of molten salts in the second-step reaction zone was set to 265° C. In Comparative Example 4, no partition was disposed and a reaction inhibition layer was used.

In the first-step reaction zone which is operated at isothermal conditions, the temperature of a hot spot was 407.9° C., and the yields of acrolein and acrylic acid were 80.92% and 9.09%, respectively. In the second-step reaction zone which is operated at isothermal conditions, the yields of acrolein and acrylic acid were 0.807% and 84.21%, respectively.

$T_{h1} - T_{salt1}$ was 107.9° C.

COMPARATIVE EXAMPLE 5

A Case Where Each of Reaction Zones is Filled with Catalysts Having the Same Activity: Changes in Hot Spot Temperature and Yield with Change in Setting Temperature of Molten Salt Comparative Example 5 was performed in the same manner as in Comparative Example 4 except for the setting temperature of molten salts in each of the reaction zones. The temperature of molten salts in each of the reaction zone was set to 305° C., and the temperature of molten salts in the second-step reaction zone was set to 265° C.

In the first-step reaction zone which is operated at isothermal conditions, the temperature of a hot spot was 418.3° C., and the yields of acrolein and acrylic acid were 80.77% and 9.15%, respectively. In the second-step reaction zone which is operated at isothermal conditions, the yields of acrolein and acrylic acid were 0.934% and 84.30%, respectively.

$T_{h1} - T_{salt1}$ was 113.3° C.

COMPARATIVE EXAMPLE 6

Use of a Reaction Inhibition Layer Having a Thickness Corresponding to only 10% of the Thickness of a Partition The procedure of Example 6 was repeated except that a reaction inhibition layer having a thickness corresponding to only 10% of the thickness of a partition was inserted into a portion of the first-step catalyst layer, where the partition had been placed.

COMPARATIVE EXAMPLE 7

No Use of a Reaction Inhibition Layer

The procedure of Example 6 was repeated except that a reaction inhibition layer was not inserted into a portion of the first-step catalyst layer, where the partition had been placed.

TABLE 1

| Reaction zone | | Ex. 1 | Ex. 2 | Ex. 3 | Ex. 4 | Ex. 5 | Comp. Ex. 1 | Comp. Ex. 2 | Comp. Ex. 3 |
|---|---|---|---|---|---|---|---|---|---|
| First step | Temp. of molten salt (° C.) | 300 305 | 300 310 | 300 315 | 300 320 | 308 315 | 300 | 305 | 310 |
| | Temp. of hot spot (° C.) | 381.6 | 381.5 | 381.2 | 381.2 | 392.5 | 383.8 | 394.6 | 405.7 |
| | Acrolein | 81.17% | 81.13% | 79.01% | 78.97% | 80.33% | 81.34% | 81.91% | 80.43% |
| | Acrylic acid | 8.84% | 9.30% | 11.46% | 11.45% | 11.37% | 8.18% | 8.35% | 10.11% |
| Second step | Temp. of molten salt (° C.) | 265 | 265 | 265 | 265 | 265 | 265 | 265 | 265 |
| | Temp. of hot spot (° C.) | 327 | 320 | 327.5 | 327.0 | 320.5 | 320.1 | 320.3 | 316.0 |
| | Acrolein | 0.553% | 1.18% | 0.607% | 0.607% | 0.631% | 1.585% | 1.424% | 1.257% |
| | Acrylic acid | 84.01% | 84.35% | 84.95% | 84.88% | 86.83% | 83.11% | 84.07% | 84.66% |

TABLE 2

| Reaction zone | | Example 6 | Comparative Example 4 | Comparative Example 5 |
|---|---|---|---|---|
| First step | Temp. of molten salt (° C.) | 295 305 | 300 | 305 |
| | $T_{h1}$ (° C.) | 392.3 | 407.9 | 418.3 |
| | $T_{h2}$ (° C.) | 363.6 | — | — |
| | Δ T1 (° C.) | 97.3 | 107.9 | 113.3 |
| | Δ T2 (° C.) | 58.5 | — | — |
| | Acrolein | 79.51% | 80.92% | 80.77% |
| | Acrylic acid | 11.08% | 9.09% | 9.15% |
| Second step | Temp. of molten salt (° C.) | 265 | 265 | 265 |
| | Acrolein | 0.704% | 0.807% | 0.934% |
| | Acrylic acid | 85.54% | 84.21% | 84.30% |

TABLE 3

| Reaction zone | | Example 6 | Comparative Example 6 | Comparative Example 7 |
|---|---|---|---|---|
| First step | Temp. of molten salt (° C.) | 295 305 | 295 305 | 295 305 |
| | $T_{intf}$ (° C.) | 330.9 | 362.4 | 395.7 |
| | $T_{intf} - T_{salt1}$ (° C.) | 35.9 | 67.4 | 100.7 |
| | Acrolein | 79.51% | 81.05% | 80.77% |
| | Acrylic acid | 11.08% | 9.23% | 9.34% |
| Second step | Temp. of molten salt | 265 | 265 | 265 |
| | Acrolein | 0.704% | 0.689% | 0.654% |
| | Acrylic acid | 85.54% | 84.01% | 84.30% |

$T_{intf}$: The temperature of a catalyst layer at the position of a partition.

As apparent from the results for Comparative Examples 1 to 3, it can be found that if the first-step reaction zone is set to isothermal conditions in order to increase yield, the temperature of the molten salt must be increased, resulting in a significant increase in the temperature of the hot spot in the catalyst layer.

In Example 3, the yield of acrylic acid was higher than those of Comparative Examples 2 and 3, and also the hot spot temperature was much lower due to the application of multi-step heat control, thus making stable operations possible. As evident from the comparison between Example 2 and Comparative Example 2 having the same average temperature of molten salts in the first-step reaction (305° C.) and from the comparison between Example 4 and Comparative Example 3 (310° C.), it can be found that if the first-step reaction is conducted in the two-divided heat control zones as in examples, the final yield of acrylic acid will be higher than that of the case where the first-step reaction is performed at isothermal condition. Also, the temperature peaks of the hot spots in examples will be much lower than those of the isothermal condition case, thus making stable operations possible.

In Examples 1 to 4, as the temperature of the second shell space increased from 305° C. to 320° C., the conversion of acrolein produced in the first-step reaction zone to acrylic acid was increased so that the yield of acrolein was relatively reduced. Thus, the load of the second-step reaction zone for converting acrolein to acrylic acid was slightly reduced, thus increasing the yield of acrylic acid. In examples using multi-step heat control, a load for conversion of acrolein in the second-step reaction zone was lower than that of all comparative examples. Among them, Example 3 showed the lowest load for conversion of acrolein in the second-step reaction zone, indicating the highest final yield of acrylic acid. From the results for Examples 1–4, the sum of the yield of the intermediate products (acrolein+acrylic acid) produced in the first-step reaction zone was the highest in Example 3, indicating that Example 3 had the highest selectivity to the final product (acrylic acid).

In Example 5, the temperatures of molten salts in the shell spaces of the first-step reaction zone were set to 308° C. and 315° C. in an axial direction such that the temperature of the front portion of the first-step reaction zone was higher than that of Examples 1–4. This resulted in a higher yield than those of Examples 1–4. The temperature of the hot spot was increased to 392.5° C. due to the increase in the molten salt temperature. However, it could be found that the sums of the yields of acrolein and acrylic acid in the first-step reaction zone was 91.7% for Example 5 and 90.47% for Example 3, indicating that the conversion and selectivity to the intermediate and final products were higher in Example 5. As a result, the yield of acrylic acid in the second-step reaction zone was 86.83% which is the highest of all the experimental results.

In addition, by introducing the inactive material layer into a position where heat transfer is problematic due to the installation of the partition, an abnormal increase in temperature in the catalyst layer did not appear.

Meanwhile, as evident from the results given in Table 2, it can be found that even when the first-step reaction zone is filled with catalysts with the same activity, the effect of multi-step heat control is realized. In Example 6, multi-step heat control was applied, and in Comparative Examples 4 and 5, the first-step reaction zone was operated under isothermal condition. As apparent from Table 2, in Example 6, $\Delta T$ ($T_h - T_{salt1}$) was controlled in the specified range by multi-step heat control while yield and selectivity were better than those of Comparative Examples 4 and 5. In Comparative Examples 4 and 5, the temperature in the hot spot was a very high temperature close to the sintering temperature of the catalyst, resulting in the deterioration of catalyst and also in side reactions due to the high temperature around the hot spot, thus leading to a reduction on yield upon long-term operation. Particularly, in Comparative Examples 4 and 5 in which $\Delta T$ ($T_h - T_{salt1}$) was closed to or exceeded 110° C. which is a preferred value specified in claims 13 and 15 of the present invention, the yield of acrylic acid, a final product, was at least 1% lower than that of Example 6, due to an increase in byproducts, such as carbon dioxide, acetic acid, etc.

Table 3 shows the results of an experiment to solve a problem in that heat transfer does not sufficiently occur due to the insertion of the partition. In Example 6, the reaction inhibition layer was inserted into a position where the partition has been placed, and in this state, an experiment was performed. Comparative Example 6 was the same as in Example 6 except that the thickness of the reaction inhibition layer was 10% of the thickness of the partition. Comparative Example 7 was the same as in Example 6 except that the reaction inhibition layer was not inserted into the location of the partition. As evident from Table 3, since temperature control in the partition location where heat transfer is problematic was not easy, Comparative Example 6 showed an increase in temperature of 67.4° C. as compared to the temperature of molten salts, and Comparative Example 7 showed an increase in temperature of 100.7° C. Such increases in temperature are significantly different from that of Example 6. Also, it could be found that $T_{intf}$ (the temperature of catalyst layer at the partition location) was close to the peak temperature of the catalyst layer. It is believed that this is mainly attributed to heat accumulation by an exothermic reaction which occurs since heat transfer around the partition is not easy. If the reaction inhibition layer is not used, heat accumulation will not be the only problem. As apparent from Comparative Examples 6 and 7 where the reaction inhibition layer was not sufficiently ensured, the yield of acrylic acid, a final product, was also reduced as compared to Example 6. This indicates that reaction heat at the partition location did not easily flow out, so as to cause an abnormal increase in temperature and finally a reduction in selectivity, thus leading to an increase in the amount of byproducts.

INDUSTRIAL APPLICABILITY

As described above, the present invention provides the improved heat control system for use in the two-step process of producing unsaturated aldehydes and unsaturated acids by the oxidation of olefins. This heat control system allows the design of a reactor system to which the advantages of the prior art can be sufficiently applied even under reaction conditions with high load. If this heat control system is used, the formation of a hot spot or heat accumulation in the hot spot can be inhibited, and as a result, unsaturated aldehydes and unsaturated acids can be produced at high productivity and also the life cycle of a catalyst can be extended.

The invention claimed is:

1. In a process of producing unsaturated aldehydes and unsaturated acids from olefins by fixed-bed catalytic partial oxidation in a shell-and-tube heat exchanger-type reactor, the reactor comprising one or more catalytic tubes each including a first-step reaction zone of mainly producing the unsaturated aldehydes, a second-step reaction zone of mainly producing the unsaturated acids, or both the two zones, the improvement wherein:

the first-step reaction zone is divided into two or more zones by a partition, each of the divided shell spaces being filled with a heat transfer medium, the heat transfer medium being maintained at isothermal temperature or a temperature difference of 0–5° C., in which the temperatures of the heat transfer medium in each of the divided shell spaces are set to increase in the moving direction of reactants, and when the shell spaces divided by the partition in the first-step reaction zone are named, such as zone 1, zone 2, zone 3, . . . , $T_{h1}-T_{salt1}$ is $\leq 150°$ C. and $T_{hN}-T_{saltN}$ is $\leq 120°$ C., wherein N is an integer of 2 or more, $T_{h1}$ is the peak temperature of a reaction mixture in a catalyst layer corresponding to the first shell space (the peak temperature of the catalyst layer), $T_{hN}$ is the peak temperature of a reaction mixture in a catalyst layer corresponding to the Nth shell space (the peak temperature of the catalyst layer), $T_{salt1}$ is the temperature of a heat transfer medium filled in the first shell space, and $T_{saltN}$ is the temperature of a heat transfer medium filled in the Nth shell space.

2. In a process of producing unsaturated aldehydes and unsaturated acids from olefins by fixed-bed catalytic partial oxidation in a shell-and-tube heat exchanger-type reactor, the reactor comprising one or more catalytic tubes each including a first-step reaction zone of mainly producing the unsaturated aldehydes, a second-step reaction zone of mainly producing the unsaturated acids, or both the two zones, the improvement wherein:

the first-step reaction zone is divided into two or more zones by a partition, each of the divided shell spaces being filled with a heat transfer medium, the heat transfer medium being maintained at isothermal temperature or a temperature difference of 0–5° C., in which the temperatures of the heat transfer media in each of the divided shell spaces are set to increase in the moving direction of reactants, and a reaction inhibition layer made of an inactive material alone or a mixture of the inactive material and a catalyst is placed in a position within the catalytic tube, which corresponds to a position where the partition is disposed.

3. The process of claim 1 or 2, which is a process of producing acrolein and acrylic acid from propylene.

4. The process of claim 1 or 2, wherein the temperature difference between the heat transfer media filled in the adjacent shell spaces is in a range of 0° C.–50° C.

5. The process of claim 1 or 2, wherein the partition is disposed in such a manner that it covers at least one temperature peak.

6. The process of claim 5, wherein the temperature peak occurs at the inlet of the reactor, the front portion of each of the reaction zones, or a boundary between the adjacent catalyst layers with different activities.

7. The process of claim 1, wherein a reaction inhibition layer made of an inactive material alone or a mixture of the inactive material and a catalyst is placed in a position within the catalytic tube, which corresponds to a position where the partition is disposed.

8. The process of claim 2 or 7, wherein the volume ratio of the inactive material to the catalyst material in the reaction inhibition layer is 20–100%.

9. The process of claim 2 or 7, wherein the height of the reaction inhibition layer is 20–500% of the thickness of the partition.

10. The process of claim 1 or 2, wherein each of the reaction zones except for the inactive material layer or the reaction inhibition layer is filled with either one catalyst layer with the same activity or two or more catalyst layers with different activities, the two or more catalyst layers are being filled such that their activities increase in an axial direction.

11. The process of claim 1 or 2, wherein the temperature of the heat transfer medium filled in each of the shell spaces can be controlled independently.

12. The process of claim 1 or 2, wherein the space velocity of the olefins introduced into the reactor inlet is in a range of 50–130 $hr^{-1}$.

13. The process of claim 1 or 7, wherein $T_{h1}-T_{salt1}$ is $\leq 110°$ C., and $T_{hN}-T_{saltN}$ is $\leq 100°$ C.

14. In a shell-and-tube heat exchanger-type reactor which can be used in a process of producing unsaturated aldehydes and unsaturated acids from olefins by fixed-bed catalytic partial oxidation, the reactor comprising one or more catalytic tubes each including a first-step reaction zone of mainly producing the unsaturated aldehydes, a second-step reaction zone of mainly producing the unsaturated acids, or both the two zones, the improvement wherein: the first-step reaction zone is divided into two or more zones by a partition, each of the divided shell spaces being filled with a heat transfer medium, the heat transfer medium in each of the shell spaces being maintained at isothermal temperature or a temperature difference of 0–5° C., in which the temperatures of the heat transfer media in each of the divided shell spaces are set to increase in the moving direction of reactants, and when the shell spaces divided by the partition in the first-step reaction zone are named, such as zone 1, zone 2, zone 3, . . . , $T_{h1}-T_{salt1}$ is $\leq 150°$ C. and $T_{hN}-T_{saltN}$ is $\leq 120°$ C., wherein N is an integer of 2 or more, $T_{h1}$ is the peak temperature of a reaction mixture in a catalyst layer corresponding to the first shell space (the peak temperature of the catalyst layer), $T_{hN}$ is the peak temperature of a reaction mixture in a catalyst layer corresponding to the Nth shell space (the peak temperature of the catalyst layer), $T_{salt1}$ is the temperature of a heat transfer medium filled in the first shell space, and $T_{saltN}$ is the temperature of a heat transfer medium filled in the Nth shell space.

15. The shell-and-tube heat exchanger-type reactor of claim 14, wherein $T_{h1}-T_{salt1}$ is $\leq 110°$ C., and $T_{hN}-T_{saltN}$ is $\leq 100°$ C.

16. In a shell-and-tube heat exchanger-type reactor which can be used in a process of producing unsaturated aldehydes and unsaturated acids from olefins by fixed-bed catalytic partial oxidation, the reactor comprising one or more catalytic tubes each including a first-step reaction zone of mainly producing the unsaturated aldehydes, a second-step reaction zone of mainly producing the unsaturated acids, or both the two zones, the improvement wherein: the first-step reaction zone is divided into two or more shell spaces by a partition, each of the divided shell spaces being filled with a heat transfer medium, the heat transfer media being maintained at isothermal temperature or a temperature difference of 0–5° C., in which the temperatures of the heat transfer media in each of the divided shell spaces are set to increase in the moving direction of reactants; and a reaction inhibition layer made of an inactive material alone or a mixture of the inactive material and a catalyst is placed within a portion of the catalytic tube, which corresponds to a location where the partition is disposed.

* * * * *